United States Patent [19]

Takeuchi et al.

[11] Patent Number: 4,736,631

[45] Date of Patent: Apr. 12, 1988

[54] ULTRASONIC PROBES

[75] Inventors: Hiroshi Takeuchi, Matsudo; Chitose Nakaya; Kageyoshi Katakura, both of Tokyo, all of Japan

[73] Assignee: Hitachi, Ltd., Tokyo, Japan

[21] Appl. No.: 904,099

[22] Filed: Sep. 4, 1986

[30] Foreign Application Priority Data

Oct. 9, 1985 [JP] Japan ................................ 60-223606

[51] Int. Cl.$^4$ .............................................. G01N 29/00
[52] U.S. Cl. ..................................................... 73/649
[58] Field of Search ........................ 73/649, 662, 626; 310/336; 128/660; 367/105

[56] References Cited

U.S. PATENT DOCUMENTS 3,979,711 9/1976 Maginness et al. ............... 73/626 X
4,112,411 9/1978 Alais et al. ...................... 367/905 X
4,448,075 5/1984 Takemura et al. ................... 73/626

*Primary Examiner*—Jerry W. Myracle
*Attorney, Agent, or Firm*—Antonelli, Terry & Wands

[57] ABSTRACT

Disclosed is an ultrasonic probe which is capable of externally and selectively controlling the conversion efficiency of an electroacoustic conversion portion. For the electroacoustic conversion portion is used a material which does not exhibit or exhibit the piezoelectricity depending on the absence or the presence of bias electric field, for example, a certain kind of ferroelectric material which is maintained at a temperature in the vicinity of the phase transition temperature thereof or a material having high electrostrictive effect. The electroacoustic conversion efficiency is controlled by applying bias electric field to such a material.

7 Claims, 2 Drawing Sheets

ULTRASONIC PROBES

BACKGROUND OF THE INVENTION

The present invention relates to an ultrasonic probe used for ultrasonic diagnostic apparatus.

Ultrasonic diagnostic apparatus are known which radiate ultrasonic pulse beams into an object to be examined, receive the echoes which are reflected by the boundary of the structures of organisms in accordance with a difference in acoustic impedance, displaying them on a display such as a cathode-ray tube, and observing the structure of the organisms of the object to be examined from the displayed image of a desired tomogram. Since they enable the interior of the body to be diagnosed from the exterior, they are widely used.

An ultrasonic probe having an electroacoustic conversion element is used in order to transmit and receive ultrasonic waves. An ultrasonic exciting signal of a desired frequency is supplied to the electroacoustic conversion element, whereby ultrasonic beams are radiated from the exited element and the reflected echo is converted into an electrical signal.

Lead zirconate titanate (PZT) piezoelectric ceramic plates are conventionally widely used for the electroacoustic conversion portions. Lead zirconate titanate is a ferroelectric substance which has a spontaneous polarization, and exhibits strong piezoelectricity when the polarities are aligned in perpendicular to the ceramic plate by applying a strong electric field perpendicularly to the ceramic plate surface at a predetermined temperature, namely, by poling. Since a PZT ceramic exhibits ferroelectricity up to the temperature limit which is sufficiently higher than room temperature and has strong coercive field, remanent polarization after poling is retained stably. Therefore, even if the ambient temperature changes or electric field is applied, the piezoelectricity of a PZT ceramic hardly changes unless there is a great change in the ambient temperature or the electric field. A conventional ultrasonic probe obtains stable electroacoustic conversion efficiency utilizing this characteristic.

With a recent demand for a higher-capacity ultrasonic diagnostic apparatus, however, it is sometimes desirable to externally control the conversion characteristic of the electroacoustic conversion portion of an ultrasonic probe. For example, in a conventional electronically scanning linear array ultrasonic probe shown in FIG. 1, the ultrasonic beam pattern viewed in the direction of array (in the longitudinal direction L) of each of the strip-shaped transducer elements 12 held by a backing member 11 is controlled by varying the number of transducer elements to be driven (in this case, the aperture of the linear array probe) and the phase of an electrical signal to be applied.

However, since the aperture and, hence, the position of the focal point is fixed with respect to the direction (transverse direction S) perpendicular to the direction of array (longitudinal direction L) of the transducer elements, it is impossible to control the resolution in the transverse direction S. Therefore, it is sometimes impossible to obtain sufficient resolution according to particular positions (probing depths) of objects to be examined. This problem is solved by weighting the distribution of the conversion efficiency by externally controlling the electroacoustic conversion efficiency in each transducer element, but this solution is difficult with respect to the above-described transducer element made of a PZT piezoelectric ceramic.

A method for solving this problem is disclosed in Japanese Patent Laid-Open No. 21057/1981. In this method, each of the electrodes on the upper and lower surfaces of the transducer elements are divided in the longitudinal and transverse directions, so that the aperture in the transverse direction of the probe is also variable. The effects brought about by this method, however, may be insufficient, because, even if a driving electric field is selectively applied to each divided electrode on the upper and lower surfaces of electroacoustic conversion elements, the vicinities thereof may also be excited by a leakage electric field.

SUMMARY OF THE INVENTION

Accordingly, it is an object of the present invention to provide an ultrasonic probe which is capable of selectively and externally controlling the conversion efficiency of an electroacoustic conversion portion, thereby eliminating the above-described problems in the prior art.

To achieve this aim, in view of the fact that a ferroelectric piezoelectric material does not exhibit or exhibits the ferroelectricity (piezoelectricity) depending on the absence or the presence of bias electric field when the temperature is maintained in the vicinity of the phase transition temperature, and the fact that a material having high electrostrictive effect can induce large piezoelectricity when a bias electric field is applied to it, these materials are used for the electroacoustic conversion portion of an ultrasonic probe according to the present invention and the electroacoustic conversion efficiency is controlled by the bias electric field applied to these materials. Furthermore, according to the present invention, weight distribution is provided for the electroacoustic conversion efficiency by providing an electric field distribution for the electroacoustic conversion portion, thereby enabling the ultrasonic beam pattern to be controlled.

The above and other objects, features and advantages of the present invention will become clear from the following description of the preferred embodiments thereof, taken in conjunction with the accompanying drawings.

DESCRIPTION OF THE PREFERRED EMBODIMENTS

Embodiment of the present invention will be described hereinunder.

Figure 1:
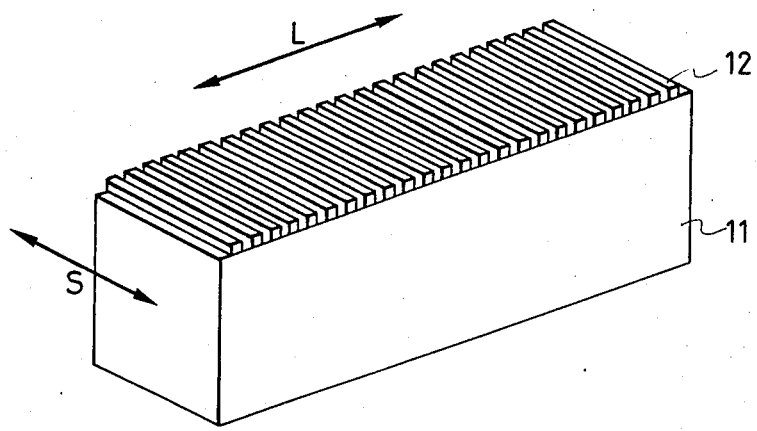
FIG. 1 shows the structure of the main part of a conventional ultrasonic probe.
Figure 2:
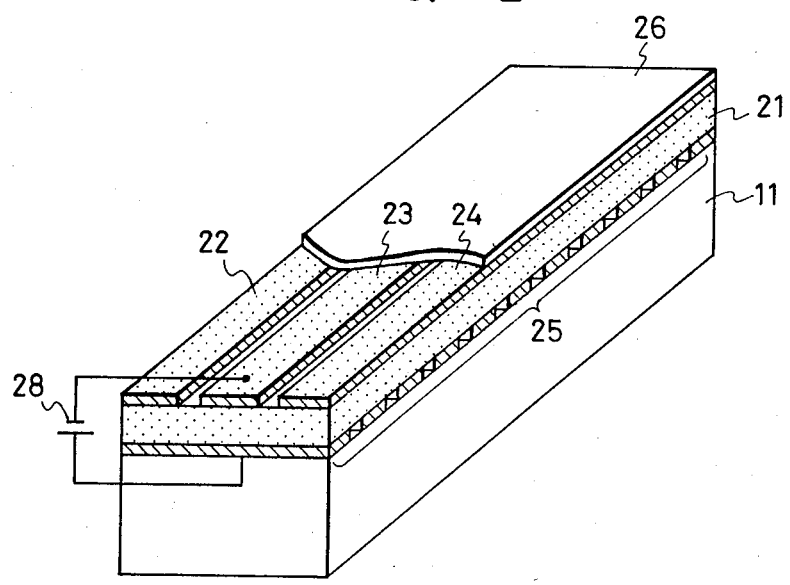
FIG. 2 shows the structure of an embodiment of an ultrasonic probe according to the present invention.

Referring now to FIG. 2, the structure of an embodiment of the present invention is shown. A lanthanum-doped lead zirconate titanate $Pb(Zr_{0.65}Ti_{0.035})O_3$, what is called a PLZT ceramic, is used as a ferroelectric material having a comparatively low phase transition temperature for a ferroelectric piezoelectric material, for example, of less than 100° C. If 8.5 mol % of L is doped with respect to Pb, phase transistion is observed in the vicinity of 40° C. This material exhibits ferroelectricity, spontaneous polarization and piezoelectricity at 40° C. or lower, but at more than 40° C., the spontaneous polarization and piezoelectricity thereof disappears. However, even at more than 40° C., the application of bias electric field induces ferroelectricity and, hence, piezoelectricity.

One surface of a rectangular plate 21 which is made of a piezoelectric ceramic such as that shown in FIG. 2 is divided into three parts so as to make ground electrodes 22, 23 and 24, and a hot electrode array 25 is formed on the other side. The rectangular plate 21 is adhered to the backing material 11 with the hot electrode array 25 faced downward, and an acoustic matching layer 26 is provided on the ground electrodes 22, 23 and 24, so that an electronically scanning linear array ultrasonic probe is obtained. If such an ultrasonic probe is maintained at a temperature of 40° C., piezoelectric activity is shown at the portion at which the hot electrode is opposed to a particular ground electrode only while a DC bias electric field is applied between the hot electrode and the ground electrode. For example, if the ground electrode 23 alone is used and bias electric field is applied to the hot electrode 25, the portion corresponding to the width of the ground electrode 23 becomes piezoelectric active with respect to the transverse direction. Therefore, if a pulse electric field with a DC bias electric field 28 applied thereto is applied betweenthe hot electrode 25 and the ground electrode 23, an ultrasonic pulse is radiated mainly from the portion which corresponds to the width of the ground electrode 23 with respect to the transverse direction. If all the ground electrodes 22, 23 and 24 are used, an ultrasonic pulse is radiated from the portion which corresponds to the total transverse width of the probe. In other words, it is possible to effectively vary the transverse aperture of the probe by selecting the ground electrode to be used.

Experiments on formation of ultrasonic beams were made using the electronically scanning linear array ultrasonic probe shown in FIG. 2 and maintaining the temperature at more than 40° C. As a result, it was found that if the ground electrode 23 alone is used, the width of the ultrasonic beam as viewed in the transverse direction is comparatively narrower at a short distance than that produced when using all the ground electrodes. This is considered to be because the effective transverse aperture of the probe is smaller. In other words it was confirmed that the ultrasonic beam pattern viewed in the transverse direction is controlled by varying the distribution of the bias electric field.

Figure 3:
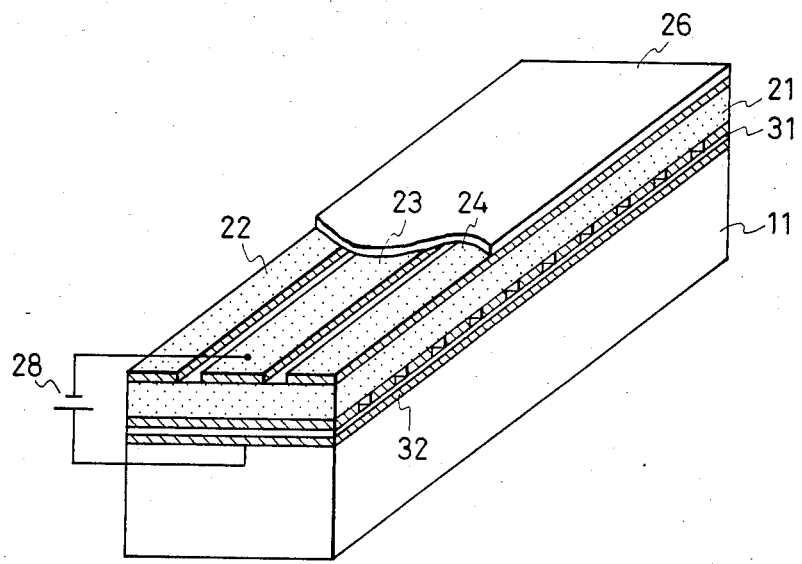
FIG. 3 shows the structure of another embodiment of an ultrasonic probe according to the present invention.

FIG. 3 shows the structure of another embodiment of the present invention.

A barium strontium titanate (Ba, Sr)TiO$_3$ ceramic is used as a material having high electrostrictive effect. This ceramic can induce high piezoelectricity when a bias electric field is applied to it. Using this material, an ultrasonic probe can be constructed in the same way as in the first embodiment. That is, one surface of the ceramic rectangular plate 21 is divided into three parts so as to make ground electrodes 22, 23 and 24, and a hot electrode array 25 is formed on the other side. In this embodiment, the resulting ultrasonic probe exhibits similar functions and effects as described in connection with the first embodiment. Therefore, similarly to the first embodiment, it is possible to effectively vary the transverse aperture of the probe by applying the bias electric field 28 to the hot electrode and selecting the ground electrode to be used.

Although the ground electrode is divided into three in the above-described embodiments, it is to be understood that the number is not limited to three but the electrode may be divided into any given number.

The aim of the present invention is also achieved by using another means for applying the bias electric field (FIG. 3). An electrode 32 for applying the bias electric field is provided in place of the hot electrode 25 according to the above embodiments on the hot electrode side through an insulating layer 31, separately from the ground electrodes 22 to 24, so that bias electric field is applied between this electrode 32 and the ground electrodes 22, 23 and 24.

In the illustrated embodiments, the phase transition temperature is set in the vicinity of 40° C. in consideration of, in particular, medical ultrasonic diagnostic apparatus, but the present invention is not limited to the medical apparatus but is adaptable to other field, so that it is not necessary to limit the phase transition temperature to less than 40° C.

Although the aforementioned embodiments show that an electronically scanning linear array ultrasonic probe having a variable transverse aperture is realized, it is clear that according to the present invention, not only such an ultrasonic probe but a probe which is capable of controlling ultrasonic beams is generally realized by providing a given bias electric field distribution for an electroacoustic conversion portion and weighting the distribution of electroacoustic conversion efficiency as desired.

Figure 4:
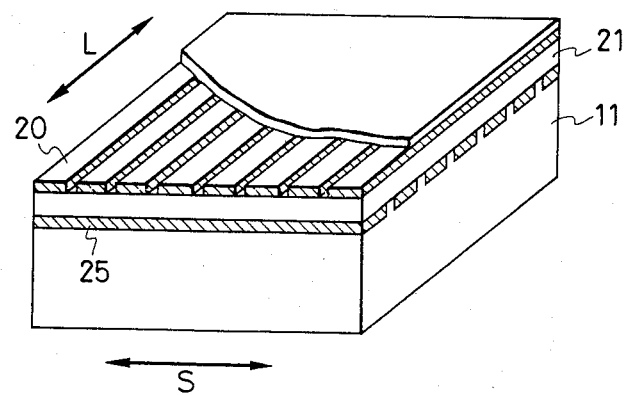
FIG. 4 shows the structure of still another embodiment of the present invention.

For example, as shown in FIG. 4, which shows the structure of still another embodiment, an electroacoustic conversion portion is composed of a ground electrode array 20 which is longitudinally divided into a plurality of ground electrodes and is formed on one surface of the plate 21, and the hot electrode array 25 which is transversely arrayed and is divided into a plurality of electrodes. An appropriate bias electric field, for example, two-dimensional electric field distribution is applied between each ground electrode 20 and hot electrode 25, so that ultrasonic beams are controlled with a given weighted distribution provided for the electroacoustic conversion efficiency of the conversion portion. Thus, the two-dimensional array ultrasonic probe shown in FIG. 4 is realized.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. An ultrasonic probe comprising:
   an ultrasonic vibrator including an electroacoustic conversion element responsive to a bias electric field for inducing piezoelectricity;
   a first electrode array including a plurality of first electrodes arranged on a first surface of said electroacoustic conversion element;
   a second electrode array including a plurality of second electrodes arranged on a second surface of said electroacoustic conversion element; and
   means for exciting said electroacoustic element including means for supplying a pulse voltage superposed by the bias electric field between at least one selected first electrode from said first electrode array and at least one selected second electrode from said second electrode array.

2. An ultrasonic probe according to claim 1, wherein said electroacoustic conversion element comprises a ferroelectric piezoelectric material for inducing piezoelectricity by the bias electric field when the ferroelectric piezoelectric material is maintained at a temperature in the vicinity of the phase transition temperature thereof.

3. An ultrasonic probe according to claim 1, wherein said electroacoustic conversion element comprises a material having an electrostrictive effect for inducing piezoelectricity.

4. An ultrasonic probe according to claim 1, wherein said electroacoustic conversion element delimits a plurality of conversion elements, said means for supplying the pulse voltage superposed by the bias electric field includes means for providing a predetermined bias electric field distribution to each of said plurality of conversion elements so as to weight the electroacoustic conversion efficiency of said electroacoustic conversion element.

5. An ultrasonic probe according to any one of claims 1, 2, 3 and 4 wherein said electroacoustic conversion element delimits an array of a plurality of strip-shaped conversion elements.

6. An ultrasonic probe according to any one of claims 1, 2, 3 and 4 wherein said electroacoustic conversion element delimits an array of a plurality of strip-shaped conversion elements, and said means for supplying the pulse voltage superposed by the bias electric field controls an electric field distribution which is perpendicular to the direction of the array of said strip-shaped conversion elements.

7. An ultrasonic probe according to any one of claims 1, 2, 3 and 4, wherein said electroacoustic conversion element delimits an array of a plurality of strip-shaped conversion elements corresponding to the first electrode array arranged on the first surface of said electroacoustic conversion element, said second electrode array being arranged in a direction transverse to the direction of said first electrode array.

* * * * *